United States Patent
Zhang et al.

(10) Patent No.: US 9,849,145 B2
(45) Date of Patent: Dec. 26, 2017

(54) PHARMACEUTICAL COMPOSITION CONTAINING HONEYSUCKLE EXTRACT AND ANTIBIOTICS, PHARMACEUTICAL KIT, AND USE OF HONEYSUCKLE EXTRACT FOR PREPARATION OF DRUG

(75) Inventors: Tiejun Zhang, Tianjin (CN); Jiangong Shi, Beijing (CN); Hong Meng, Jinan (CN); Fengnian Han, Shijiazhuang (CN); Xuwei Ma, Shijiazhuang (CN); Zhulan Li, Wuwei (CN)

(73) Assignee: Hankang Biochemical & Pharmaceutical Co., Ltd, Shijiazhuang (CN)

( * ) Notice: Subject to any disclaimer, the term of this patent is extended or adjusted under 35 U.S.C. 154(b) by 364 days.

(21) Appl. No.: 14/238,448

(22) PCT Filed: Aug. 12, 2011

(86) PCT No.: PCT/CN2011/078331
§ 371 (c)(1),
(2), (4) Date: Feb. 11, 2014

(87) PCT Pub. No.: WO2013/023338
PCT Pub. Date: Feb. 21, 2013

(65) Prior Publication Data
US 2014/0193530 A1    Jul. 10, 2014

(51) Int. Cl.
| *A61K 36/355* | (2006.01) |
| *A61K 36/36* | (2006.01) |
| *A61K 31/7048* | (2006.01) |
| *C07H 17/04* | (2006.01) |
| *A61K 31/428* | (2006.01) |
| *A61K 31/7042* | (2006.01) |

(52) U.S. Cl.
CPC ........ *A61K 31/7048* (2013.01); *A61K 31/428* (2013.01); *A61K 31/7042* (2013.01); *A61K 36/355* (2013.01); *C07H 17/04* (2013.01)

(58) Field of Classification Search
CPC ............................. A61K 36/36; A61K 36/355
USPC .................................................. 424/778, 779
See application file for complete search history.

(56) References Cited

U.S. PATENT DOCUMENTS 4,281,061 A * 7/1981 Zuk ...................... G01N 33/542
435/188

FOREIGN PATENT DOCUMENTS

| CN | 1969960 A | 5/2007 |
| CN | 101085795 A | * 12/2007 |
| WO | WO 2010/102830 A2 | 9/2010 |

OTHER PUBLICATIONS

Chen, Yiqiang et al., "In vitro effects of honeysuckle aqueous-extracts alone and in combination with ceftzidime on *Pseudomonas aeruginosa* biofilm", Chinese Journal of Microbiology and Immunology, Sep. 2004, vol, 24, No. 9, pp. 10, 15, 19, and 23 and abstract.*

Chen, Yiqiang et al., "In vitro effects of honeysuckle aqueous-extracts alone and in combination with ceftzidime on *Pseudomonas aeruginosa* biofilm," Chinese Journal of Microbiology and Immunology, Sep. 2004, vol. 24, No. 9, English translation of pp. 10, 15, 19, 23, and Abstract.

Dong, I. C. et al., "Effects of resveratrol-related hydroxystilbenes on the nitric oxide production in macrophage cells: structural requirements and mechanism of action," *Life Sciences*, 2002, vol. 71, pp. 2071-2082.

English Translation of Abstract of CN 1969960 A (1 page).
English Translation of Abstract of WO 2010/102830 A2 (1 page).
English Translation of the detailed description of CN 101085795 A (9 pages).

International Search Report dated Mar. 22, 2012 for application PCT/CN2011/078331, with English Translation (8 pages).

Qin, Xuejun, "Inhibitory and Destructive Effect of Honeysuckle Aqueous Extracts on Biofilm Formation by *Pseudomonas aeruginosa* in Vitro," *China Master's Theses Full-Text Database*, Jul. 8, 2003, English translation of Abstract (8 pages).

Wu, Bin et al., "Efficacy observation on reduning injection and antibiotic treatment for community acquired pneumonia requiring hospitalization," *Chinese Journal of Modern Drug Application*, Apr. 2011, vol. 5, No. 8, English translation of Abstract (5 pages).

Zhang, Xiaoguang, "Chemical Studies on the Water-soluble Fraction extracted from Flos Lonicerae Japonicae," *China Master's Theses Full-Text Database*, Aug. 8, 2007, English translation of Abstract (2 pages).

* cited by examiner

*Primary Examiner* — Chris R Tate
*Assistant Examiner* — Deborah Davis
(74) *Attorney, Agent, or Firm* — Lewis Roca Rothgerber Christie LLP

(57) ABSTRACT

Provided is a pharmaceutical composition useful for prevention and/or treatment of diseases caused by bacteria, wherein the pharmaceutical composition comprising a honeysuckle extract containing iridoid compounds and an antibiotic. Also provided is a pharmaceutical kit comprising the honeysuckle extract containing the iridoid compounds and the antibiotics which are separately placed. The honeysuckle extract is used in combination with the antibiotics, the responsiveness of multi-drug resistant bacteria to antibiotics is improved, a clinical application prospect is presented, especially the current status of the refractory bacterial infection diseases caused by the pathogenic bacteria resistant to the antibiotics can be improved. Also provided is a use of the pharmaceutical composition and pharmaceutical kit in the preparation of drugs for prevention and/or treatment a diseases caused by bacteria. In addition, also provided is a use of the honeysuckle extract in the preparation of drugs for reversing bacterial resistance.

8 Claims, 3 Drawing Sheets

PHARMACEUTICAL COMPOSITION CONTAINING HONEYSUCKLE EXTRACT AND ANTIBIOTICS, PHARMACEUTICAL KIT, AND USE OF HONEYSUCKLE EXTRACT FOR PREPARATION OF DRUG

CROSS-REFERENCE TO A RELATED APPLICATION(S)

This application is a National Phase Patent Application and claims priority to and benefit of International Patent Application Number PCT/CN2011/078331, filed on Aug. 12, 2011, the entire disclosure of which is incorporated herein by reference.

TECHNICAL FIELD

The present invention belongs to the technical field of pharmaceutics. Specifically, the present invention relates to a pharmaceutical composition containing an antibiotic and a honeysuckle extract which is prepared by extracting from traditional Chinese medicine of honeysuckle, its original plant of *lonicera japonica* or congeneric plants and purifying, and a use of the pharmaceutical composition in the preparation of drugs for preventing and/or treating diseases caused by bacteria. In addition, the present invention also relates to a use of the honeysuckle extract for preparation of drugs.

BACKGROUND

In recent years, the problem of intensive use of a large number of antibiotics in medical practice has become increasingly serious. Improper use of antibiotics exerts a selective evolutionary pressure on microorganisms, especially bacteria, resulting in a sharp increase in the number and species of resistant bacteria, even causing a "superbug" which can resist a variety of antibiotics. In general, most new antibiotics will lose their original efficacy within a number of years due to appearance of drug resistance of pathogens. For example, penicillin-resistant *Streptococcus pneumoniae* is very sensitive to drugs such as penicillin, erythromycin and sulfanilamide in the past, but is almost ineffective now. For another example, common sources of infection such as *Staphylococcus aureus*, *Streptococcus pneumoniae*, Genus *Enterococcus* and *Pseudomona aeruginosa* gradually become multi-resistant, and have resistances to the commonly used β-lactams, quinolinone, novel macrolides and cephalosporins, even vancomycin. For yet another example, data indicate that resistances of *Pseudomonas aeruginosa* to eight antibiotics such as amoxicillin and zinacef reach 100%, and resistances of *Klebsiella pneumoniae* to 16 high-grade antibiotics such as zinacef and fortum reach up to 51.85-100%. While methicillin-resistant *Staphylococcus aureus* can only be cured by vancomycin.

Generation of a large number of resistant bacteria brings about more and more intractable infections, resulting in increasingly more risks of bacterial infection and increasingly more costs on treatment of infectious diseases. How to reduce resistance of bacteria to antibiotics and increase sensitivity of bacteria to antibiotics has become a problem of great concern in the medical field.

The name of Chinese traditional herb "Honeysuckle" originates from "Compendium of Materia Medica", and is the general designation of Chinese herbs and plants. The honeysuckle of plants is also known as *lonicera japonica*, which is a perennial semi-evergreen twining woody liana of caprifoliaceae. *Lonicera japonica* is named as honeysuckle owing to blooming initially white flower, and then changing into yellow flower. Honeysuckle of herbs is the plant of *lonicera japonica* of *lonicera linn* in caprifoliaceae and dried buds or primal flowers of congeneric plants.

Honeysuckle has been praised as excellent medicine with heat-clearing and detoxifying effect since ancient times, which is one of medicines commonly used for heat-clearing and detoxifying in traditional Chinese medicine. Since thousands of years, honeysuckle has been playing a prominent effect in clinic, and well-loved in the doctor and patient populations. Honeysuckle, sweet in taste, cold in nature and having aromatic scent, can clear heat without hurting stomach, and not only has aromatic scent but also can eliminate pathogenic factors. Honeysuckle not only can dissipate wind-heat, but also is good at detoxification of blood, and is therefore used for treating various febrile diseases such as fever, eruption, skin patch, heat toxic swelling sore, and sore throat and the treatment effect is significant. Modern research preliminarily discusses the heat-clearing and detoxifying mechanisms of honeysuckle. For example, honeysuckle has significant antipyretic and anti-inflammatory effects, intraperitoneal injection of 0.25 g/kg honeysuckle extract can inhibit rat swollen feet caused by carrageenan; injection of 30-40 g/kg honeysuckle extract can alleviate degree of egg white foot swelling; and injection of 8 g/kg honeysuckle extract twice a day also has significant anti-exudative and anti-proliferative effects on rat croton oil granuloma pouch. It is also considered that honeysuckle has important regulatory effect on body immune system, and honeysuckle decoction promotes the phagocytosis of white blood cells; intraperitoneal injection of honeysuckle also has significant effect on promoting phagocytosis of inflammatory cells.

Studies on the chemical compositions of honeysuckle show that, honeysuckle contains organic acids, triterpenoid saponins, flavonoids and glycosides thereof, iridoid glycosides, volatile oils and so on. Research has been carried out currently to extract the active ingredients of honeysuckle and prove their efficacy, but so far, there has been no report of enhancing the sensitivity of bacteria to antibiotics by using honeysuckle extract in combination with antibiotics.

SUMMARY

It is an object of the present invention to provide a pharmaceutical composition containing a honeysuckle extract and an antibiotic. Wherein the honeysuckle extract is prepared by extracting from honeysuckle, its original plants of *lonicera japonica* or other congeneric plants, with secologanic acid as its active ingredient.

It is another object of the present invention to provide a pharmaceutical kit comprising a honeysuckle extract and an antibiotic which are separately placed.

It is yet another object of the present invention to provide a use of the pharmaceutical composition and pharmaceutical kit in the preparation of drugs for preventing and/or treating a disease caused by a bacterium.

It is still yet another object of the present invention is to provide a use of a honeysuckle extract containing iridoid compounds in the preparation of drugs for reversing resistance of bacteria.

The technical solutions of the present invention are as follows:

In one aspect, the present invention provides a pharmaceutical composition for preventing and/or treating a disease caused by a bacterium, the pharmaceutical composition comprises a honeysuckle extract containing iridoid compounds and an antibiotic.

Preferably, the pharmaceutical composition further comprises a pharmaceutically acceptable carrier and/or excipient.

Wherein preventing and/or treating a disease caused by a bacterium is achieved by reversing resistance of bacteria. Therefore, when bacteria develop resistance to antibiotics, the pharmaceutical composition can reverse or confront the drug resistance of bacteria.

In another aspect, the present invention provides a pharmaceutical kit for preventing and/or treating a disease caused by a bacterium, the pharmaceutical kit comprises a honeysuckle extract containing iridoid compounds and an antibiotic which are placed separately. The kit can be used for preventing and/or treating a disease caused by a bacterium in a patient in need thereof, wherein the honeysuckle extract and antibiotic may be administered to a patient simultaneously, continuously or sequentially at a time interval. Experiments show that the honeysuckle extract can enhance, restore and/or improve the sensitivity of bacteria to antibiotics, and reverse and confront resistance of bacteria to antibiotics, thereby enhancing effects of antibiotics on killing or inhibiting bacteria.

In the above pharmaceutical composition and pharmaceutical kit, the honeysuckle extract contains iridoid compounds represented by the following structural formulas:

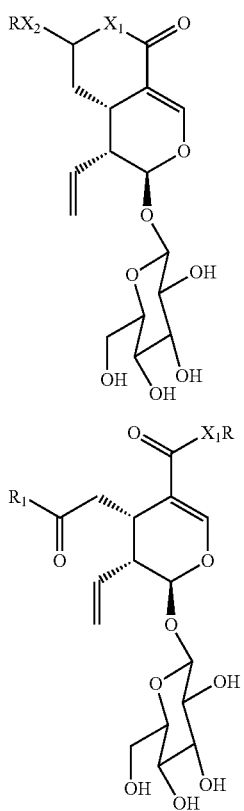

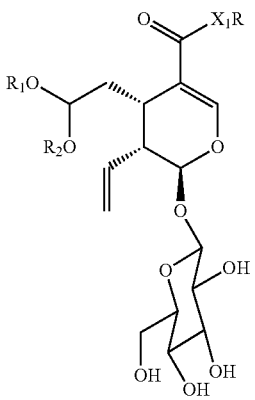

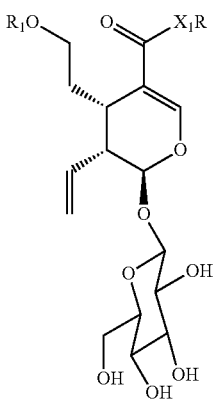

Wherein in formula (1), $X_1$ and $X_2$ each independently represent O, and R represents H, the compound is secologanic acid;

In formula (2), formula (3) and formula (4), $X_1$ and $X_2$ each independently represent H, lower alkyl of $C_{1-6}$ or lower alkenyl of $C_{2-6}$.

The main active ingredient of the honeysuckle extract is secologanic acid.

Preferably, the honeysuckle extract contains 50 wt % or more of secologanic acid; preferably, the honeysuckle extract contains 70 wt % or more of secologanic acid; more preferably, the honeysuckle extract contains 80 wt % or more of secologanic acid; and most preferably, the honeysuckle extract contains 90 wt % or more of secologanic acid.

The honeysuckle extract of the present invention can be prepared according to the method disclosed in the patent ZL200610083556.7, which is incorporated herein by reference in its entirety. According to embodiments of the present invention, the honeysuckle extract is prepared by a method comprising the following steps:

(1) pulverizing honeysuckle of plants, its original plant of *lonicera japonica* or other congeneric plants, and then performing extraction with water and/or $C_1$-$C_6$ alkyl alcohol aqueous solution containing not more than 95% alcohol by volume to obtain an extract;

(2) concentrating and drying the extract obtained in step (1) under normal or reduced pressure to obtain an extractum, or performing spray-drying on the extract obtained in step (1) to obtain power, and dissolving the extractum or power with water, then carrying out precipitation or settlement with $C_1$-$C_6$ alkyl alcohol aqueous solution containing not more than 95% alcohol by volume to obtain a precipitate or a dissolving liquid concentrate;

(3) isolating and purifying the precipitate or dissolving liquid concentrate obtained in step (2) by chromatography, and collecting eluent containing iridoid compounds, wherein the chromatography is selected from one or more of macroporous adsorption resin column chromatography, normal phase silica gel chromatography and reversed phase silica gel chromatography;

preferably, the honeysuckle extract is prepared by a method comprising the following steps:

(1) pulverizing honeysuckle herbs and then performing extraction with 50% (v/v) ethanol aqueous solution to obtain an extracted liquid;

(2) concentrating the extracted liquid obtained in step (1) under reduced pressure to obtain an extractum, dissolving the extractum with water, filtering, and concentrating the solution to dryness, and performing dissolution by adding 95% (v/v) ethanol aqueous solution, and adding distilled water to make the solution contain 75% (v/v) ethanol, filtering after standing, and recovering ethanol from the filtrate to obtain a fluid extractum;

(3) dissolving the fluid extractum obtained in step (2) by adding water and filtering to obtain a filtrate, and making the filtrate pass through a styrene macroporous adsorption resin chromatographic column, and then eluting the column sequentially with water and 20% (v/v) ethanol aqueous solution, and recovering ethanol in the eluent of 20% (v/v) ethanol aqueous solution;

more preferably, the method further comprises the step of purifying the eluent containing iridoid compounds obtained in step (3) by gel chromatography;

most preferably, the method further comprises the step of purifying the eluent containing iridoid compounds obtained in step (3) by Sephadex LH-20 gel chromatographic column and collecting the eluent of water.

Preferably, the antibiotic of the present invention is selected from one or more of the group consisting of ampicillin, penam sulfone, piperacillin, tazobactam, amoxicillin, clavulanic acid, cefazolin, cefuroxime, ceftriaxone, cefuroxime sodium, sulperazon, left-handed oxygen fluorine, cefotaxime, ceftazidime, imipenem, cefepime, cefoxitin, gentamicin, amikacin, ciprofloxacin, chloramphenicol, trimethoprim-sulfamethoxazole, tetracycline, nitrofurantoin, aztreonam, ciprofloxacin, norfloxacin, ammonia, sulbactam, ticarcillin, clavulanic acid, tobramycin, tazocin, imipenem, minocycline, meropenem, penicillin, oxacillin, erythromycin, vancomycin, rifampin and clindamycin.

Preferably, the antibiotic is ampicillin and/or erythromycin.

In another aspect, the present invention provides a use of the pharmaceutical composition and pharmaceutical kit in the preparation of drugs for preventing and/or treating a disease caused by a bacterium.

Preferably, the bacterium may be an antibiotic-resistant bacterium, preferably multiple antibiotic-resistant bacterium; more preferably, the bacterium may be a multiple antibiotic-resistant gram-negative bacterium; further preferably, the multiple antibiotic-resistant gram-negative bacterium is selected from one or more of the group consisting of *Escherichia coli, Pseudomona aeruginosa, Klebsiella pneumoniae, Acinetobacter baumannii, Proteus bacillus*, enterobacteriaceae, *Haemophilus influenzae*, pneumobacillus and catarrhalis; more preferably, the multiple antibiotic-resistant gram-negative bacterium is *Escherichia coli, Pseudomona aeruginosa* and/or *Klebsiella pneumoniae*.

Alternatively, the bacterium is a multiple antibiotic-resistant gram-positive bacterium; preferably, the multiple antibiotic-resistant gram-positive bacterium may be selected from one or more of the group consisting of *Staphylococcus aureus*, methicillin-resistant *Staphylococcus aureus*, Group A *Streptococcus pyogenes, Streptococcus pneumoniae, Bacillus subtilis* and *Staphylococcus epidermidis*; further preferably, the multiple antibiotic-resistant gram-positive bacterium is methicillin-resistant *Staphylococcus aureus* and/or *Staphylococcus aureus*.

In addition, in the use according to the present invention, the disease caused by a bacterium is an infectious disease caused by a bacterium, especially the infectious diseases caused by antibiotic-resistant bacteria, such as digestive system infection; blood system infection; respiratory system infection; urinary tract infection; central nervous system infection; bone and joint infection; ear, mastoid and sinus infection; and skin and soft tissue infection; preferably, the disease caused by a bacterium is respiratory system infection caused by the antibiotic-resistant bacterium.

Wherein the disease caused by a bacterium may be respiratory system infection caused by a multiple antibiotic-resistant gram-negative bacterium; preferably, the disease caused by a bacterium is infectious pneumonia caused by a multiple antibiotic-resistant gram-negative bacterium; further preferably, the disease caused by a bacterium is nosocomial infectious pneumonia caused by a multiple antibiotic-resistant gram-negative bacterium; more preferably, the disease caused by a bacterium is nosocomial infectious pneumonia caused by a multiple antibiotic-resistant *Klebsiella pneumoniae*.

Alternatively, the disease caused by a bacterium may be respiratory system infection caused by a multiple antibiotic-resistant gram-positive bacterium; preferably, the disease caused by a bacterium is pneumonia caused by a multiple antibiotic-resistant gram-positive bacteria; further preferably, the disease caused by a bacterium is pneumonia caused by methicillin-resistant *Staphylococcus aureus*.

In yet another aspect, the present invention also provides a use of a honeysuckle extract containing iridoid compounds in the preparation of drugs for reverting resistance of bacteria. Experiments show the honeysuckle extract can enhance, restore and/or improve the sensitivity of bacteria to antibiotics, and thereby can be used in the preparation of drugs for reverting and confronting resistance of bacteria. The drug, when administered to the patient, can revert or confront resistance of resistant bacteria (even multiple antibiotic-resistant bacteria) in the body of a patient to antibiotics, and can also prevent bacteria in the body of a patient from developing resistance to antibiotics.

Wherein the honeysuckle extract contains iridoid compounds represented by the following structural formulas:

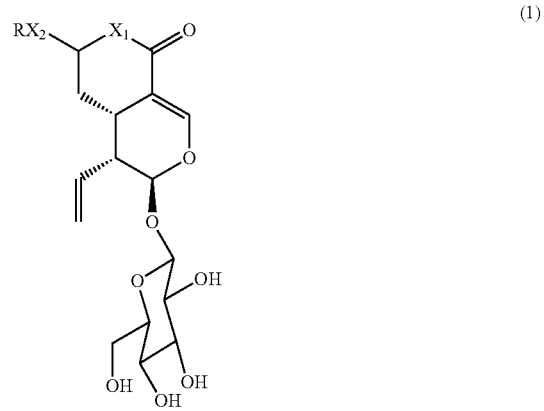

(1)

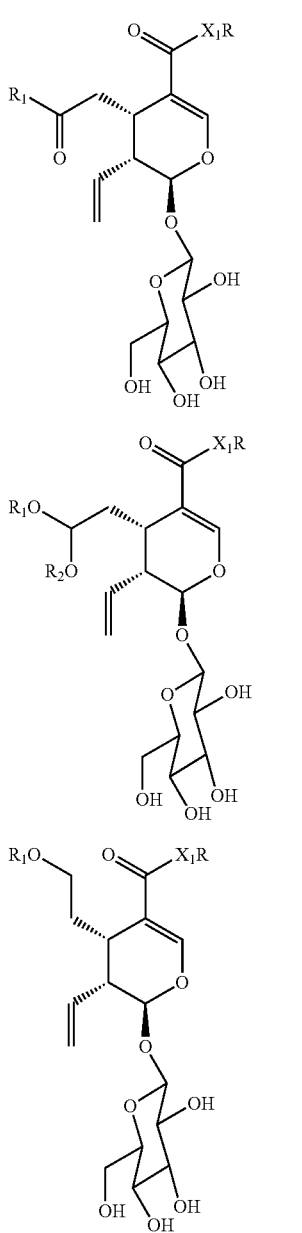

(2)

(3)

(4)

Wherein in formula (1), $X_1$ and $X_2$ each independently represent O, and R represents H;

in formula (2), formula (3) and formula (4), $X_1$ and $X_2$ each independently represent H, lower alkyl of $C_{1-6}$ or lower alkenyl of $C_{2-6}$.

Preferably, the honeysuckle extract contains 50 wt % or more of secologanic acid represented by formula (1); further preferably, the honeysuckle extract contains 70 wt % or more of secologanic acid; more preferably, the honeysuckle extract contains 80 wt % or more of secologanic acid; and most preferably, the honeysuckle extract contains 90 wt % or more of secologanic acid.

The honeysuckle extract of the present invention can be prepared according to the method disclosed in the patent ZL200610083556.7, which is incorporated herein by reference in its entirety. According to embodiments of the present invention, the honeysuckle extract is prepared by a method comprising the following steps:

(1) pulverizing honeysuckle of plants, its original plant of *lonicera japonica* or other congeneric plants, and then performing extraction with water and/or $C_1$-$C_6$ alkyl alcohol aqueous solution containing not more than 95% alcohol by volume to obtain an extract;

(2) concentrating the extract obtained in step (1) under normal or reduced pressure to obtain an extractum, or performing spray-drying on the extract obtained in step (1) to obtain power, and dissolving the extractum or power with water, then carrying out precipitation or settlement with $C_1$-$C_6$ alkyl alcohol aqueous solution containing not more than 95% alcohol by volume to obtain a precipitate or a dissolving liquid concentrate;

(3) isolating and purifying the precipitate or dissolving liquid concentrate obtained in step (2) by chromatography, and collecting eluent containing iridoid compounds, wherein the chromatography is selected from one or more of macroporous adsorption resin column chromatography, normal phase silica gel chromatography and reversed phase silica gel chromatography;

preferably, the honeysuckle extract is prepared by a method comprising the following steps:

(1) pulverizing honeysuckle herbs with 50% (v/v) ethanol aqueous solution to obtain an extracted liquid;

(2) concentrating the extracted liquid obtained in step (1) under reduced pressure to obtain an extractum, dissolving the extractum with water, filtering, and concentrating the solution to dryness, and performing dissolution by adding 95% (v/v) ethanol aqueous solution, and adding distilled water to make the solution contain 75% (v/v) ethanol, filtering after standing, and recovering ethanol from the filtrate to obtain a fluid extractum;

(3) dissolving the fluid extractum obtained in step (2) by adding water and filtering to obtain a filtrate, and making the filtrate pass through a styrene macroporous adsorption resin chromatographic column, and then eluting the column sequentially with water and 20% (v/v) ethanol aqueous solution, and recovering ethanol in the eluent of 20% (v/v) ethanol aqueous solution;

more preferably, the method further comprises the step of purifying the eluent containing iridoid compounds obtained in step (3) by gel chromatography;

most preferably, the method further comprises the step of purifying the eluent containing iridoid compounds obtained in step (3) by Sephadex LH-20 gel chromatographic column and collecting the eluent of water.

In the use according to the present invention, the resistance of bacteria is resistance of bacteria to antibiotics;

preferably, the resistance of bacteria is resistance of bacteria to multiple antibiotics;

further preferably, the antibiotic of the present invention is selected from one or more of the group consisting of ampicillin, penam sulfone, piperacillin, tazobactam, amoxicillin, clavulanic acid, cefazolin, cefuroxime, ceftriaxone, cefuroxime sodium, sulperazon, left-handed oxygen fluorine, cefotaxime, ceftazidime, imipenem, cefepime, cefoxitin, gentamicin, amikacin, ciprofloxacin, chloramphenicol, trimethoprim-sulfamethoxazole, tetracycline, nitrofurantoin, aztreonam, ciprofloxacin, norfloxacin, ammonia, sulbactam, ticarcillin, clavulanic acid, tobramycin, tazocin, imipenem, minocycline, meropenem, penicillin, oxacillin, erythromycin, vancomycin, rifampin and clindamycin.

Preferably, the antibiotic is ampicillin and/or erythromycin.

In addition, the drug may further contain an antibiotic; preferably, the antibiotic is selected from one or more of the group consisting of ampicillin, penam sulfone, piperacillin, tazobactam, amoxicillin, clavulanic acid, cefazolin, cefuroxime, ceftriaxone, cefuroxime sodium, sulperazon, left-handed oxygen fluorine, cefotaxime, ceftazidime, imipenem, cefepime, cefoxitin, gentamicin, amikacin, ciprofloxacin, chloramphenicol, trimethoprim-sulfamethoxazole, tetracycline, nitrofurantoin, aztreonam, ciprofloxacin, norfloxacin, ammonia, sulbactam, ticarcillin, clavulanic acid, tobramycin, tazocin, imipenem, minocycline, meropenem, penicillin, oxacillin, erythromycin, vancomycin, rifampin and clindamycin; further preferably, the antibiotic is ampicillin and/or erythromycin.

After the chlorogenic acid and its derivatives are considered to have anti-bacterial and anti-viral activity, basic researches on substances of honeysuckle having heat-clearing and detoxifying effect set off a climax, a number of research institutes or laboratories are dedicated to the isolation and extraction of the active ingredients of honeysuckle.

Through a large number of experiments, the present inventors extracted a honeysuckle extract mainly containing secologanic acid from honeysuckle herbs and purified the extract, and found in the effect experiments combining antibiotics that, the honeysuckle extract could significantly enhance, restore and/or improve sensitivity of multiple resistant bacteria to antibiotics, and reverse or confront resistance of multiple resistant bacteria to antibiotics, which is embodied in that, the antibiotic which loses its original antibacterial efficacy due to resistance of bacteria restores its effect of inhibiting bacteria by adding the honeysuckle extract under the same level of antibiotics, thus proving that the honeysuckle extract can restore or improve sensitivity of resistant bacteria to antibiotics, and therefore can be used for adjuvant therapy of infectious diseases caused by resistant bacteria.

BRIEF DESCRIPTION OF THE DRAWINGS

Hereinafter, the examples of the present invention will be illustrated in detail in combination with the accompanying draws.

DETAILED DESCRIPTION OF THE EMBODIMENTS

The present invention will be further described in detail below in conjunction with the specific embodiments, and the examples provided are only intended to illustrate the present invention rather than limit the scope of the present invention.

The experimental methods in the following examples are all conventional methods unless expressly stated. The experimental materials such as medicinal materials and reagent materials used in the following examples can be purchased from conventional biochemical reagent stores or pharmaceutical trading enterprises unless expressly stated. Wherein:

Honeysuckle herbs employed in the examples were purchased from Beijing Tongrentang chain drug stores, produced in the province of Henan, and processed by Bozhou City Beijing Anhui Chinese Medicine Yinpian Factory, with lot number of 200502014. The honeysuckle herbs were identified as dried buds of *Lonicera japonica Thunb.* of caprifoliaceae by Institute of Materia Medica, Chinese Academy of Medical Sciences.

Figure 6:
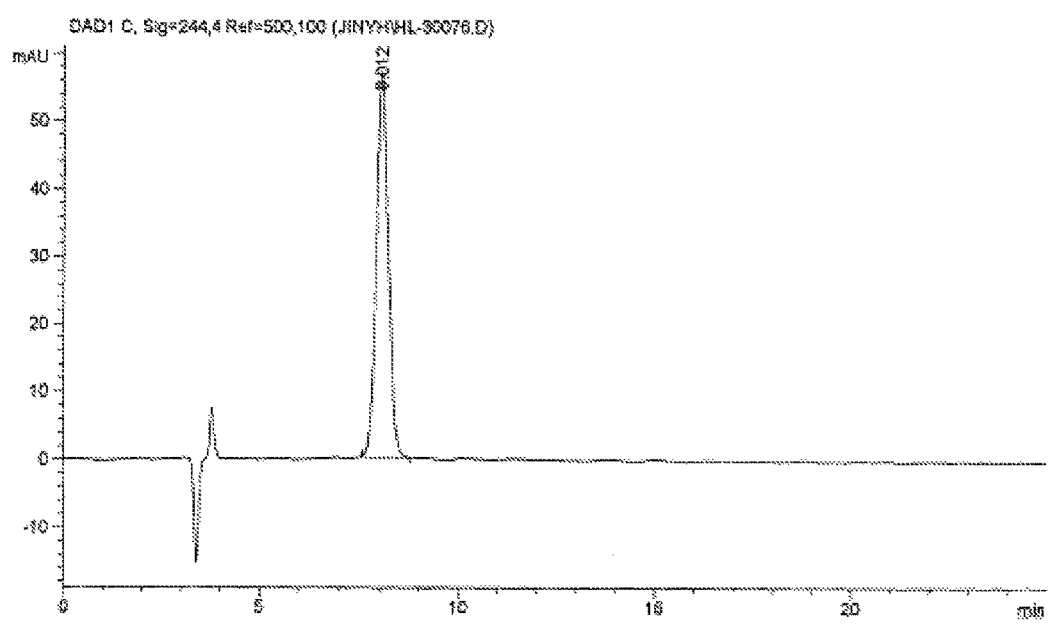
FIG. 6 shows an HPLC chromatogram of secologanic acid standard employed in the example of the present invention, with a purity of 98.03% (by weight).

The secologanic acid used in the examples, as the standard for determining the content of the extract, is prepared according to the method disclosed in the patent ZL200610083556.7 by Research Department of Natural Medicinal Chemistry of Institute of Materia Medica, Chinese Academy of Medical Sciences. Though measurement, the content is determined to be 98.03% (the chromatogram is shown in FIG. 6).

In the examples, the content of the secologanic acid in the honeysuckle extract is determined according to the HPLC external standard method, and specifically, the following instruments and conditions are employed for measurement:

(1) Instrument: Agilent 1100 liquid chromatograph including quaternary pump, autosampler, DAD detector and Chemstation chromatography workstation;

(2) Chromatographic conditions and system suitability test: the chromatographic column is Prevail $C_{18}$ 5μ (250 mm×4.6 mm) [Alltech, USA]; acetonitrile-1% glacial acetic acid aqueous solution (13:87) is used as the mobile phase, gradient elution is employed; the flow rate is 0.9 ml/min, the stopping time is 40 minutes, the equilibrium time is 10 minutes and the detection wavelength is 242 nm. The number of theoretical plates calculated by JYH peak should be no less than 1000.

(3) Reagents: acetonitrile gradient grade for chromatography; pure water; analytical grade acetic acid.

The bacteria of *Escherichia coli, Pseudomona aeruginosa, Klebsiella pneumonia* and *Staphylococcus aureus* used in the examples are all clinical isolates (multiple resistant bacteria), which were provided by the clinical laboratory of the Fourth People's Hospital of Jinan in Shandong province, the resistances of the bacteria are shown in the tables 1, 2, 3, 4 and 5 below.

TABLE 1

Background materials of *Klebsiella pneumoniae*

| Number of specimen | Department | Date of specimen | Kind of specimen | AMP | PIP | TZP | AMC | CZO | CXM | CTX | CAZ | CRO | IPM |
|---|---|---|---|---|---|---|---|---|---|---|---|---|---|
| 31853 | Internal medicine 3 | 2010-10-29 | urine | R | I | S | S | S | S | S | S | S | S |
| | | | | FEP | FOX | GEN | AMK | CIP | CHL | SXT | TCY | NIT | |
| | | | | S | S | S | S | R | I | R | R | R | |

TABLE 2

| | | | | | | | | | | | | | | |
|---|---|---|---|---|---|---|---|---|---|---|---|---|---|---|
| Background materials of *Escherichia coli* | | | | | | | | | | | | | | |
| Number of specimen | Department | Date of specimen | Kind of specimen | AMP | PIP | TZP | AMC | CZO | CXM | CTX | CAZ | CRO | IPM |
| 32042 | Internal medicine 6 | 2010-10-29 | urine | R | R | I | I | R | R | R | R | R | S |
| | | | | FEP | FOX | GEN | AMK | CIP | CHL | SXT | TCY | NIT | |
| | | | | R | R | R | S | R | S | R | R | R | |

Notes of Table 1 and Table 2:
R: Resistant;
S: Sensitive;
I: Intermediate degree (moderate resistance).
AMP: ampicillin;
PIP: piperacillin;
TZP: piperacillin/tazobactam;
AMC: amoxicillin/clavulanic acid;
CZO: cefazolin;
CXM: cefuroxime;
CTX: cefotaxime;
CAZ: ceftazidime;
CRO: ceftriaxone;
IPM: imipenem;
FEP: cefepime;
FOX: cefoxitin;
GEN: gentamicin;
AMK: amikacin;
CIP: ciprofloxacin;
CHL: chloramphenicol;
SXT: trimethoprim-sulfamethoxazole;
TCY: tetracycline;
NIT: nitrofurantoin.

TABLE 3

| | | | | | | | | | | | |
|---|---|---|---|---|---|---|---|---|---|---|---|
| Background materials of *Pseudomona aeruginosa* | | | | | | | | | | | |
| Number of specimen | Date of specimen | AK | ATM | AMP | CRO | CLS | CXM | CAZ | CTX | CFP | CIP | CN |
| 12 | 2007-3 | S | S | R | R | S | R | S | S | S | S | S |
| | | FEP | LEV | NOR | PIP | SAM | TIM | TOB | TZP | IPM | MH |
| | | S | S | S | S | R | S | S | S | S | R |

Notes:
R: Resistant;
S: Sensitive;
I: Intermediate degree.
AK: amikacin;
ATM: aztreonam;
AMP: ampicillin;
CRO: ceftriaxone;
CLS: sulperazon;
CXM: cefuroxime sodium;
CAZ: ceftazidime;
CTX: cefotaxime;
CFP: cefoperazone;
CIP: ciprofloxacin;
CN: gentamicin;
FEP: cefepime;
LEV: left-handed oxygen fluorine;
NOR: norfloxacin;
PIP: piperacillin;
SAM: ampicillin/sulbactam;
TIM: ticarcillin/clavulanic acid;
TOB: tobramycin;
TZP: tazocin;
IPM: imipenem;
MH: minocycline;
MEM: meropenem.

TABLE 4

Background materials of *Staphylococcus aureus*

| Number of specimen | Department | Date of specimen | Kind of specimen | PNE | OXA | SAM | FOX | GEN | AMK | CIP |
|---|---|---|---|---|---|---|---|---|---|---|
| Y31692 | Surgery 4 | 2010-10-1 | secretion | R | S | S | S | S | S | S |
|  |  |  |  | ERY | VAN | RIF | SXT | TCY | CLI | NIT |
|  |  |  |  | R | S | S | S | R | R | S |

Notes:
R: Resistant;
S: Sensitive;
I: Intermediate degree.
PEN: penicillin;
OXA: oxacillin;
SAM: ampicillin/penam sulfone;
FOX: cefoxitin;
GEN: gentamicin;
AMK: amikacin;
CIP: ciprofloxacin;
ERY: erythromycin;
VAN: vancomycin;
RIF: rifampin;
SXT: trimethoprim-sulfamethoxazole;
TCY: tetracycline;
CLI: clindamycin;
NIT: nitrofurantoin.

Culture medium: MH broth.

Equipments Employed in the Examples:

Constant temperature incubator: product of Shanghai Yuejin Medical Device Factory 1.

Clean bench: product of Jinan Longhong Corporation.

Microplate reader: product of Finland Leibo Corporation.

722 spectrophotometer: product of Shanghai Precision & Scientific Instrument Co., Ltd.

−80° C. refrigerator: product of American FOMAS Corporation.

Example 1 Preparation of Honeysuckle Extract

Honeysuckle herbs (500 g) were taken, pulverized coarsely, and extracted twice with 50% (v/v) ethanol aqueous solution which is 13 times the dry weight of honeysuckle herbs, each extraction was performed for 1 hour. The extracts were combined, and concentrated under reduced pressure to obtain a thick extractum, then the extractum was added with 450 ml distilled water and dissolved by heating, then cooled to room temperature, left to stand for 24 hours and filtered to obtain a clear solution.

The clear solution was concentrated under reduced pressure to dryness, and added with 1600 ml of 95% (v/v) ethanol aqueous solution, and stirred sufficiently to be dissolved, and also the solution was slowly added with distilled water to make it contain 75% (v/v) ethanol, then left to stand for 24 hours and filtered to collect the filtrate, then ethanol was recovered from the filtrate under reduced pressure until the fluid extractum was formed.

The fluid extractum was added with 500 ml water, dissolved and filtered, then the filtrate was passed through the pretreated SP-825 styrene macroporous adsorption resin chromatographic column, and the column was eluted sequentially with 5 times the amount of the resin column volumes of water and 6 times the amount of the resin column volumes of 20% (v/v) ethanol aqueous solution, and then ethanol was recovered from the eluent under reduced pressure, until there was no alcohol flavor, and freeze-drying was performed.

Figure 1:
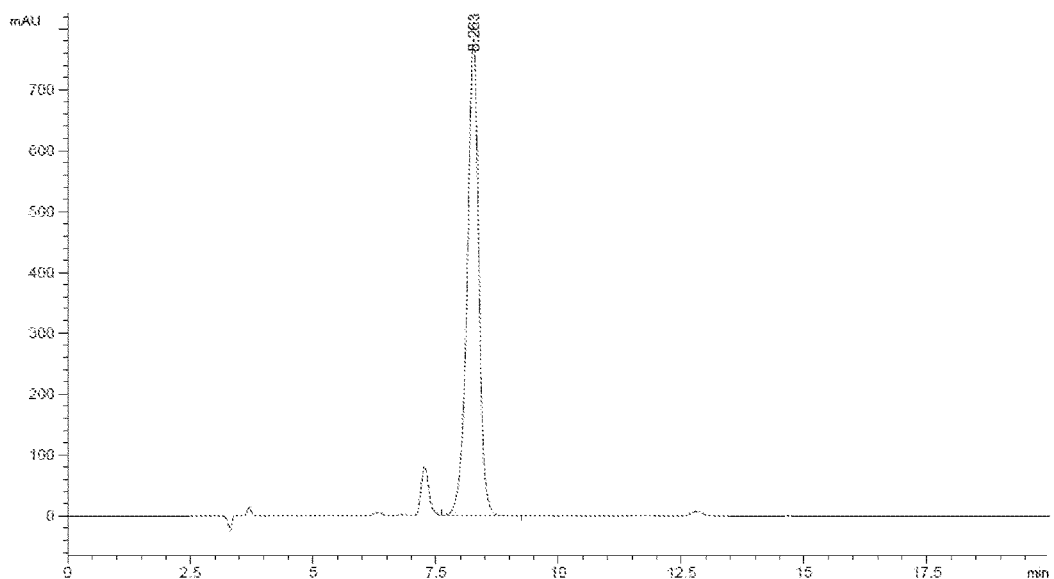
FIG. 1 shows an HPLC chromatogram of honeysuckle extract N1 prepared in Example 1 according to the present invention, which was determined to contain 90.67% (by weight) of secologanic acid.
Figure 2:
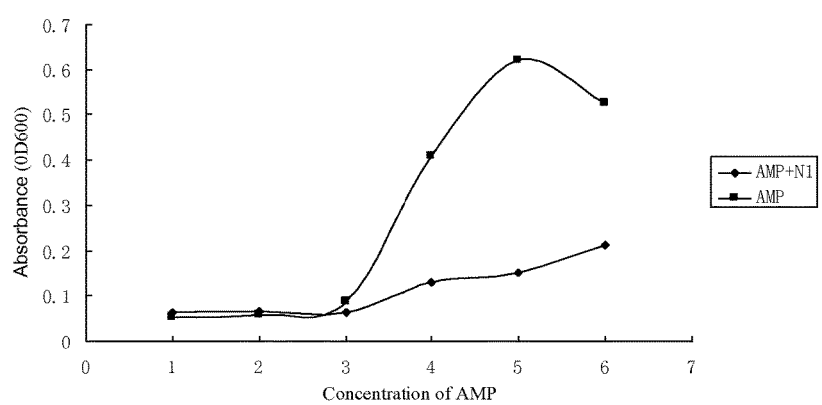
FIG. 2 shows experimental results of improving sensitivity of *Klebsiella pneumoniae* to the antibiotic "ampicillin" by using the honeysuckle extract.
Figure 3:
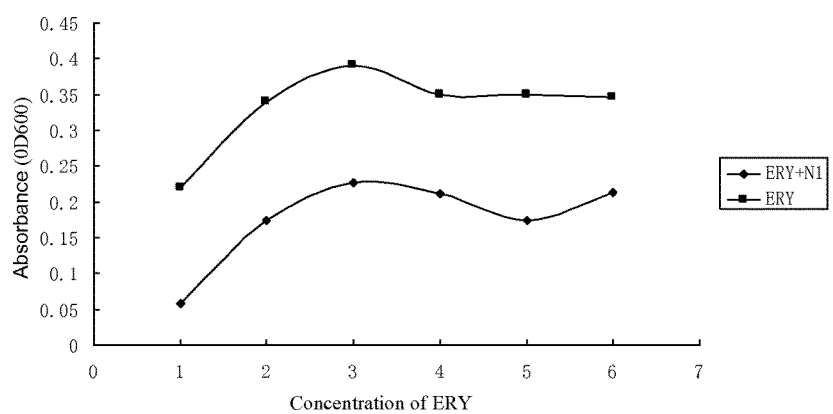
FIG. 3 shows experimental results of improving sensitivity of *Staphylococcus aureus* to the antibiotic "erythromycin" by using the honeysuckle extract.
Figure 4:
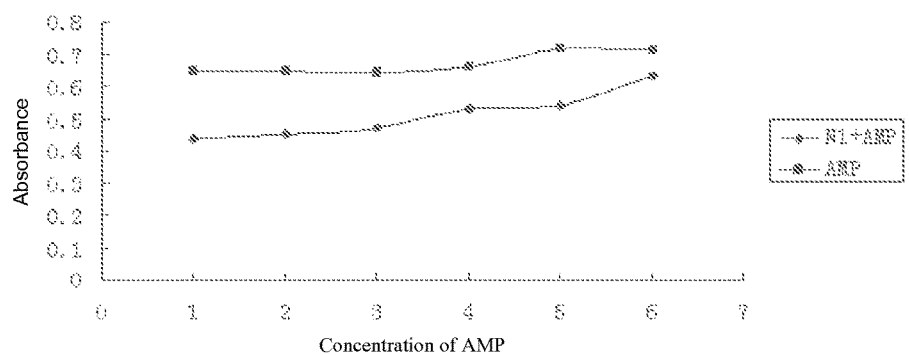
FIG. 4 shows experimental results of improving sensitivity of *Escherichia coli* to the antibiotic "ampicillin" by using the honeysuckle extract.
Figure 5:
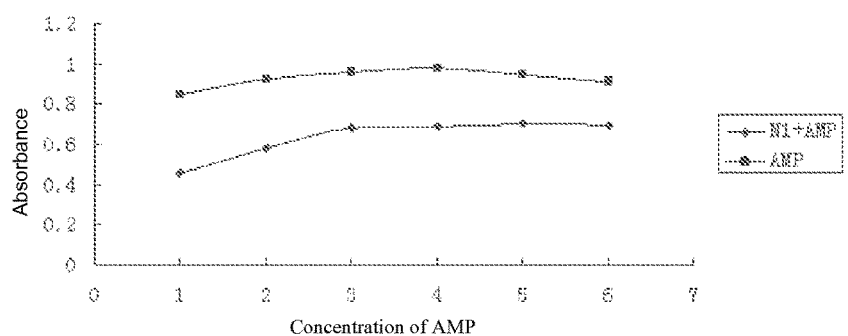
FIG. 5 shows experimental results of improving sensitivity of *Pseudomona aeruginosa* to the antibiotic "ampicillin" by using the honeysuckle extract.

Further purification was performed using Sephadex LH-20 gel chromatographic column, comprising: eluting with water, collecting the sample liquid, recovering under reduced pressure, and performing freeze-drying; and the purification was performed several times through the gel chromatographic column to obtain the honeysuckle extract N1. The honeysuckle extract N1 was determined to contain 90.67% secologanic acid according to the HPLC external standard method by using secologanic acid as the reference object (the chromatogram is shown in FIG. 1).

Example 2 Bacterial Inhibition Test of Antibiotics

In this example, bacterial inhibition effects of antibiotics on the four multiple resistant bacteria in Tables 1-4 were measured.

The activated bacterium suspension was diluted to a concentration equivalent to 0.5 McFarland turbidity standard, and diluted with the culture medium of MH broth in a proportion of 1:1000, and then added into each well in amount of 100 µL per well.

The antibiotics resisted by the above four multiple resistant bacteria were diluted to 1:2048 ($2^{-11}$) from 1 mg/mL (initial concentration) by 2-fold dilution, and then the original solution and different concentrations of diluted antibiotics were added respectively into the well containing the bacterium suspension, with each well added with 100 µL, and the minimum inhibitory concentration (MIC) of each antibiotic was recorded finally.

Meanwhile, a bacterium solution control (that is, bacterium solution plus an equal volume of culture medium) and a blank culture medium control were set.

Cultivation was performed at 37° C. for 20 h, and detection was performed at 630 nm by the microplate reader, and the bacterial inhibition rate is calculated according to formula ②, and the data obtained is put into formula ① to calculate specific distance, and the specific distance is added to the virus dilution index with pathologic rate less than 50% to obtain half inhibitory concentration (Reed-Muench method).

Specific distance=(inhibition rate of greater than 50%−50%)/(inhibition rate of greater than 50%−inhibition rate of less than 50%)    formula ①

Inhibition rate=(bacterial inhibition test OD value−drug control OD value)/(bacterium solution control OD value−blank control OD value)    formula ②

The results show that, as to the antibiotics resisted by the above four bacteria, except the antibiotic of ampicillin resisted by *Klebsiella pneumonia*, which has inhibitory effect on *Klebsiella pneumoniae* in the first two dilutions (1 mg/mL, 0.5 mg/mL), all of antibiotics resisted by the four bacteria in each dilution are resisted by the bacteria.

Example 3 Research on Antibacterial Effect of the Pharmaceutical Composition of the Present Invention The experiment of combined effects of the following antibiotics and honeysuckle extract N1 on bacteria were carried out:

TABLE 5

Bacteria and antibiotics for the experiment of combined effects

| Bacteria | Antibiotics |
|---|---|
| *Klebsiella pneumoniae* | ampicillin |
| *Staphylococcus aureus* | erythromycin |
| *Escherichia coli* | ampicillin |
| *Pseudomona aeruginosa* | ampicillin |

The antibiotics in Table 5 were diluted to $2^{-5}$ from 1 mg/mL (initial concentration) by 2-fold dilution, and then added into the 96-well plate successively in transverse direction in amount of 100 μl per well. The antibiotic of each dilution was added into three wells. The test sample of honeysuckle extract N1 prepared in Example 1 was diluted with PBS to a concentration of 40 mg/ml, and then diluted by 2-fold serial dilution (1:2, 1:4, 1:8, 1:16, 1:32, 1:64, 1:128), followed by added into each well in amount of 100 μl per well.

Meanwhile, an antibiotic control (replacing honeysuckle extract N1 with blank culture medium), bacterium solution control and blank culture medium control were set.

Cultivation was performed at 37° C. for 20 h, and the absorbance was detected at 600 nm by a spectrophotometer.

The results are shown in FIG. 2 to FIG. 5, wherein the antibiotic in each figure was diluted to $2^{-5}$ from 1 mg/mL (initial concentration) by 2-fold dilution, therefore the abscissas 1-6 in each figure represent the concentrations of $2^{-1}$-$2^{-5}$ respectively. It can be seen from the results of the figures that, addition of the honeysuckle extract significantly enhances the sensitivity of four multiple resistant bacteria to the corresponding antibiotics, therefore the honeysuckle extract can be made into the pharmaceutical composition by mixing with the antibiotic or be administered in combination with the antibiotic, so as to be used for prevention and/or treatment of diseases caused by resistant bacteria.

Example 4 Preparation of Honeysuckle Extract and Honeysuckle Water Decoction

The honeysuckle extracts with different contents of secologanic acid and honeysuckle water decoction were prepared in this example.

(1) Preparation of Honeysuckle Extract

Honeysuckle herbs (500 g) were taken, pulverized coarsely, and extracted twice with 50% (v/v) ethanol aqueous solution which is 13 times the dry weight of honeysuckle herbs, each extraction was performed for 1 hour. The extracts were combined, and concentrated under reduced pressure to obtain a thick extractum, then the extractum was added with 450 ml distilled water and dissolved by heating, then cooled to room temperature, left to stand for 24 hours and filtered to obtain a clear solution.

The clear solution was concentrated under reduced pressure to dryness, and added with 1600 ml of 95% (v/v) ethanol aqueous solution, and stirred sufficiently to be dissolved, and also the solution was slowly added with distilled water to make it contain 75% (v/v) ethanol, then left to stand for 24 hours and filtered to collect the filtrate, then ethanol was recovered from the filtrate under reduced pressure until the fluid extractum was formed.

The fluid extractum was added with 500 ml water, dissolved and filtered, then the filtrate was passed through the pretreated SP-825 styrene macroporous adsorption resin chromatographic column, and the column was eluted sequentially with 5 times the amount of the resin column volumes of water and 6 times the amount of the resin column volumes of 20% (v/v) ethanol aqueous solution, and then ethanol was recovered from the eluent under reduced pressure, until there was no alcohol flavor, and freeze-drying was performed to obtain 4.31 g honeysuckle extract (honeysuckle extract N4).

The honeysuckle extract N4 was determined to contain 52% secologanic acid according to the HPLC external standard method by using secologanic acid as the reference (the chromatogram is shown in FIG. 7).

The honeysuckle extract N4 was further purified using the Sephadex LH-20 gel chromatographic column, comprising: eluting with water, collecting the sample liquid, recovering under reduced pressure, and performing freeze-drying; and the resulting product was purified several times through the gel chromatographic column to obtain the honeysuckle extracts N3 (2.80 g, which contains 79.3% secologanic acid with chromatogram shown in FIG. 8), N2 (2.55 g, which contains 84.7% secologanic acid, with chromatogram shown in FIG. 9) and N1 (2.40 g, which contains 90.67% secologanic acid, with chromatogram shown in FIG. 10) respectively. The above concentrations were measured according to the HPLC external standard method by using secologanic acid as the reference.

(2) Preparation of Honeysuckle Water Decoction

Honeysuckle herbs (500 g) were taken, pulverized, and added with 5000 ml water, and decocted in the water, until the herb solution was evaporated to 500 ml, so that 1 g/ml crude drug was contained in the herb solution which was named honeysuckle water decoction W.

Example 5 Research on Antibacterial Effects of the Honeysuckle Extracts N1 to N4 and Honeysuckle Water Decoction W Prepared by the Present Invention which are Respectively Combined with Antibiotics This example studies the antimicrobial effects in vivo of the honeysuckle extracts N1 to N4 which are respectively combined with antibiotics, and the antimicrobial effects were compared with that of the honeysuckle water decoction W combined with the antibiotic.

The experimental strain is *Klebsiella pneumoniae* which was isolated from the sputum specimen of the patient in the ward of the Fourth People's Hospital of Jinan in 2010, and detection of the drug resistant spectrum is shown in Table 6 below.

TABLE 6

Drug resistant spectrum of the experimental strain of *Klebsiella pneumoniae*

| Number of specimen | Department | Date of specimen | Kind of specimen | AMP | PIP | TZP | AMC | CZO | CXM | CTX | CAZ | CRO | IPM |
|---|---|---|---|---|---|---|---|---|---|---|---|---|---|
| 31494 | Surgery 6 | 2010-10-11 | Sputum | R | R | I | I | R | R | R | S | R | S |

| FEP | FOX | GEN | AMK | CIP | CHL | SXT | TCY | NIT |
|---|---|---|---|---|---|---|---|---|
| S | S | R | S | R | R | R | R | R |

Notes:
R: Resistant;
S: Sensitive;
I: Intermediate degree (moderate resistance).
AMP: ampicillin;
PIP: piperacillin;
TZP: piperacillin/tazobactam;
AMC: amoxicillin/clavulanic acid;
CZO: cefazolin;
CXM: cefuroxime;
CTX: cefotaxime;
CAZ: ceftazidime;
IPM: imipenem;
FEP: cefepime;
FOX: cefoxitin;
GEN: gentamicin;
AMK: amikacin;
CIP: ciprofloxacin;
CHL: chloramphenicol;
SXT: trimethoprim-sulfamethoxazole;
TCY: tetracycline;
NIT: nitrofurantoin.

The control strain is clinically isolated AMP-sensitive strain, which was isolated from the sputum specimen of the patient in the ward of the Fourth People's Hospital of Jinan in 2010, and preserved until today.

KM mice were purchased from the Experimental Animal Center of Shandong University, weighing 16-18 g, with half male and half female and animal license number of SCXK (Lu) 20090001.

Grouping of Animals:

There were 5 control groups with 10 mice in each group: normal control group, AMP-sensitive bacterium quality control model control group (AMPS) and the treatment group thereof, AMP-resistant bacterium model control group (AMPR) and the treatment group thereof;

There were 15 experimental groups with 10 mice in each group: N1 to N4 and W were respectively combined with AMP high-dose group, AMP medium-dose group and AMP low-dose group. Doses of administration are shown in Table 7 below.

TABLE 7

Administration conditions and doses of animals in each group (n = 10)

| Groups | Dose of administration (per mouse) |
|---|---|
| Normal control group | Sterile normal saline |
| AMP-sensitive bacterium infection model control group | Sterile normal saline |
| AMP-sensitive bacterium infection model-AMP intervention control group (quality control) | AMP 16.80 mg |
| AMP-resistant bacterium infection model control group | Sterile normal saline |
| AMP-resistant bacterium infection model-AMP intervention control group | AMP 16.80 mg |
| N1-AMP high-dose group | 16.80 mg ampicillin sodium + 0.80 mg N1 |
| N1-AMP medium-dose group | 16.80 mg ampicillin sodium + 0.45 mg N1 |
| N1-AMP low-dose group | 16.80 mg ampicillin sodium + 0.10 mg N1 |
| N2-AMP high-dose group | 16.80 mg ampicillin sodium + 0.80 mg N2 |
| N2-AMP medium-dose group | 16.80 mg ampicillin sodium + 0.45 mg N2 |
| N2-AMP low-dose group | 16.80 mg ampicillin sodium + 0.10 mg N2 |
| N3-AMP high-dose group | 16.80 mg ampicillin sodium + 0.80 mg N3 |
| N3-AMP medium-dose group | 16.80 mg ampicillin sodium + 0.45 mg N3 |
| N3-AMP low-dose group | 16.80 mg ampicillin sodium + 0.10 mg N3 |
| N4-AMP high-dose group | 16.80 mg ampicillin sodium + 0.80 mg N4 (equal to 93 mg crude drug in whole) |
| N4-AMP medium-dose group | 16.80 mg ampicillin sodium + 0.45 mg N4 (equal to 52 mg crude drug in whole) |

TABLE 7-continued

Administration conditions and doses of animals in each group (n = 10)

| Groups | Dose of administration (per mouse) |
|---|---|
| N4-AMP low-dose group | 16.80 mg ampicillin sodium + 0.10 mg N4 (equal to 12 mg crude drug in whole) |
| W-AMP high-dose group | 16.80 mg ampicillin sodium + 0.093 ml W (equal to 93 mg crude drug in whole) |
| W-AMP medium-dose group | 16.80 mg ampicillin sodium + 0.052 ml W (equal to 52 mg crude drug in whole) |
| W-AMP low-dose group | 16.80 mg ampicillin sodium + 0.012 ml W (equal to 12 mg crude drug in whole) |

After being grouped, the animals were injected intraperitoneally with $2.5 \times 10^7$ (*Klebsiella pneumoniae*)*100 $\mu L^{-1}$ per animal, then immediately treated by administration, and the route of administration alternated between tail intravenous injection and intraperitoneal injection (the sterile normal saline was used as the solvent for drugs except W, since continuous tail intravenous injection causes damage to tail veins, therefore the tail intravenous injection and intraperitoneal injection were performed alternatively), the animal was injected once a day for 5 days continuously. The efficacy of each group was evaluated according to the animal mortality and intraperitoneal bacterial count.

Results of Experiment:

1: Mortalities of the Animals are Shown in Table 8 Below.

TABLE 8

Death condition of animals in each group

| | Number of deaths | | | | | | |
|---|---|---|---|---|---|---|---|
| | $1^{st}$ day | $2^{nd}$ day | $3^{rd}$ day | $4^{th}$ day | $5^{th}$ day | Total | Mortality (%) |
| Normal control group | 0 | 0 | 0 | 0 | 0 | 0 | 0 |
| AMP-resistant bacterium infection model control group | 0 | 9 | 0 | 0 | 0 | 9 | 90 |
| AMP-resistant bacterium infection model-AMP intervention control group | 0 | 7 | 2 | 1 | 0 | 10 | 100 |
| AMP-sensitive bacterium infection model control group | 0 | 9 | 1 | 0 | 0 | 10 | 100 |
| AMP-sensitive bacterium infection model-AMP intervention control group | 0 | 0 | 0 | 0 | 0 | 0 | 0 |
| N1-AMP high-dose group | 0 | 0 | 1 | 0 | 0 | 1 | 10 |
| N1-AMP medium-dose group | 0 | 0 | 0 | 0 | 0 | 0 | 0 |
| N1-AMP low-dose group | 0 | 4 | 1 | 0 | 0 | 5 | 50 |
| N2-AMP high-dose group | 0 | 1 | 1 | 0 | 0 | 2 | 20 |
| N2-AMP medium-dose group | 0 | 2 | 0 | 0 | 0 | 2 | 20 |
| N2-AMP low-dose group | 0 | 4 | 1 | 0 | 0 | 5 | 50 |
| N3-AMP high-dose group | 0 | 1 | 2 | 0 | 0 | 3 | 30 |
| N3-AMP medium-dose group | 0 | 2 | 1 | 0 | 0 | 3 | 30 |
| N3-AMP low-dose group | 0 | 4 | 2 | 0 | 0 | 6 | 60 |
| N4-AMP high-dose group | 0 | 2 | 1 | 0 | 0 | 3 | 30 |
| N4-AMP medium-dose group | 0 | 2 | 1 | 0 | 0 | 3 | 30 |
| N4-AMP low-dose group | 0 | 5 | 3 | 0 | 0 | 8 | 80 |
| W-AMP high-dose group | 0 | 4 | 4 | 0 | 0 | 8 | 80 |
| W-AMP medium-dose group | 0 | 4 | 4 | 1 | 0 | 9 | 90 |
| W-AMP low-dose group | 0 | 4 | 5 | 0 | 0 | 9 | 90 |

Analysis on results of Table 3: as can be seen from Table 3, mortalities of animals in the AMP-resistant bacterium infection model control group and AMP-sensitive bacterium infection model control group are above 90%, indicating that the models are constructed successfully. Meanwhile, the animals in the AMP-sensitive bacterium infection model-AMP intervention control group are protected effectively, while the animals in the AMP-resistant bacterium infection model-AMP intervention control group cannot be protected (all of animals died), indicating that the experimental system was normal.

As can be seen from the above results, when N1 to N4 and W were used in combination with AMP, N1 to N4 can effectively enable the animals of the experimental AMP-resistant bacterium infection model to avoid death, indicating that the test sample changes the sensitivity of experimental bacteria to antibiotics, wherein N1 has the most prominent effect. In contrast, combination of W and AMP has the worst effect, with high mortality of model animals, therefore substantially having no effect of changing sensitivity of bacteria to antibiotics.

2: Intraperitoneal Colony Counting of Animals

Intraperitoneal bacterium counting of dead animals: the animals were injected intraperitoneally with 1 ml sterile normal saline immediately after they died, and the abdomens of the animals were kneaded gently for 1 min, the ascites was drawn and coated on the plate after gradient dilution, and cultured at 37° C. overnight, then the colonies were counted;

Intraperitoneal bacterium counting of surviving animals: the mice were administrated continuously for 5 days and sacrificed through dislocation 2 h after the last administration, then the mice were injected intraperitoneally with 1 ml sterile normal saline, and the abdomens of the mice were kneaded gently for 1 min, the ascites was drawn and coated on the plate after gradient dilution, and cultured at 37° C. overnight, then the colonies were counted, colony count results of the control groups are shown in table 9 below, and colony count results of the experimental groups are shown in table 10 below.

TABLE 9

Intraperitoneal colony count of animals

| Nos. | Normal control group | AMP-sensitive bacterium (AMPS) infection model control group | AMP-sensitive bacterium (AMPS) infection model-AMP intervention control group | AMP-resistant bacterium (AMPR) infection model control group | AMP-resistant bacterium (AMPR) infection model-AMP intervention control group |
|---|---|---|---|---|---|
| 1 | 0 | $3.774 \times 10^{10}$ | $1.054 \times 10^{1}$ | $3.450 \times 10^{10}$ | $3.557 \times 10^{10}$ |
| 2 | 0 | $3.105 \times 10^{10}$ | 0 | $3.300 \times 10^{10}$ | $3.478 \times 10^{10}$ |
| 3 | 0 | $4.086 \times 10^{10}$ | 0 | $3.537 \times 10^{10}$ | $3.578 \times 10^{10}$ |
| 4 | 0 | $3.948 \times 10^{10}$ | 0 | $3.483 \times 10^{10}$ | $3.487 \times 10^{10}$ |
| 5 | 0 | $3.511 \times 10^{10}$ | 0 | $3.300 \times 10^{10}$ | $3.550 \times 10^{10}$ |
| 6 | 0 | $9.560 \times 10^{9}$ | 0 | $3.375 \times 10^{10}$ | $3.373 \times 10^{10}$ |
| 7 | 0 | $8.994 \times 10^{9}$ | 0 | $7.667 \times 10^{9}$ | $3.360 \times 10^{10}$ |
| 8 | 0 | $4.258 \times 10^{9}$ | 0 | $9.833 \times 10^{9}$ | $6.617 \times 10^{9}$ |
| 9 | 0 | $7.220 \times 10^{9}$ | 0 | $5.950 \times 10^{9}$ | $4.800 \times 10^{9}$ |
| 10 | 0 | $6.614 \times 10^{9}$ | 0 | $6.500 \times 10^{3}$ | $5.467 \times 10^{9}$ |
| Bacterium isolation positive rate (%) | 0 | 100 | 10 | 100 | 100 |

As can be seen from Table 9, the mouse infection model of the ampicillin-sensitive bacteria is sensitive to ampicillin, while the mouse infection model of the resistant bacteria cannot be controlled by ampicillin, and experimental system is normal.

TABLE 10

Intraperitoneal colony count of animals

| Nos. | N1-AMP high-dose group | N1-AMP medium-dose group | N1-AMP low-dose group | N2-AMP high-dose group | N2-AMP medium-dose group | N2-AMP low-dose group |
|---|---|---|---|---|---|---|
| 1 | $6.480 \times 10^{9}$ | 0 | $2.327 \times 10^{10}$ | $6.480 \times 10^{9}$ | $7.349 \times 10^{9}$ | $1.394 \times 10^{10}$ |
| 2 | 0 | 0 | $2.475 \times 10^{10}$ | $7.167 \times 10^{9}$ | $6.191 \times 10^{3}$ | $2.652 \times 10^{10}$ |
| 3 | 0 | 0 | $5.143 \times 10^{9}$ | $6.341 \times 10^{3}$ | $5.276 \times 10^{2}$ | $9.226 \times 10^{9}$ |
| 4 | 0 | 0 | $5.312 \times 10^{9}$ | 0 | $6.217 \times 10^{2}$ | $8.958 \times 10^{8}$ |
| 5 | 0 | 0 | $6.133 \times 10^{8}$ | 0 | 0 | $1.239 \times 10^{9}$ |
| 6 | 0 | 0 | $4.333 \times 10^{2}$ | 0 | 0 | $6.240 \times 10^{2}$ |
| 7 | 0 | 0 | $8.833 \times 10^{1}$ | 0 | 0 | 0 |
| 8 | 0 | 0 | 0 | 0 | 0 | 0 |

TABLE 10-continued

Intraperitoneal colony count of animals

| | | | | | | |
|---|---|---|---|---|---|---|
| 9 | 0 | 0 | 0 | 0 | 0 | 0 |
| 10 | 0 | 0 | 2 | 0 | 0 | 0 |
| Bacterium isolation positive rate (%) | 20 | 0 | 70 | 30 | 40 | 60 |

| | Groups | | | | | | | | |
|---|---|---|---|---|---|---|---|---|---|
| Nos. | N3-AMP high-dose group | N3-AMP medium-dose group | N3-AMP low-dose group | N4-AMP high-dose group | N4-AMP medium-dose group | N4-AMP low-dose group | W-AMP high-dose group | W-AMP medium-dose group | W-AMP low-dose group |
| 1 | $6.361 \times 10^9$ | $2.677 \times 10^{10}$ | $3.739 \times 10^{10}$ | $5.221 \times 10^9$ | $3.259 \times 10^{10}$ | | $9.773 \times 10^9$ | $3.694 \times 10^{10}$ | $3.609 \times 10^{10}$ |
| 2 | $1.165 \times 10^{10}$ | $3.534 \times 10^{10}$ | $3.841 \times 10^{10}$ | $1.478 \times 10^{10}$ | $2.299 \times 10^{10}$ | $3.916 \times 10^{10}$ | $2.340 \times 10^{10}$ | $3.715 \times 10^{10}$ | $3.480 \times 10^{10}$ |
| 3 | $9.330 \times 10^9$ | $7.992 \times 10^8$ | $9.215 \times 10^9$ | $2.468 \times 10^{10}$ | $4.761 \times 10^{10}$ | $1.643 \times 10^{10}$ | $8.216 \times 10^9$ | $3.829 \times 10^{10}$ | $8.641 \times 10^9$ |
| 4 | $8.062 \times 10^3$ | $6.749 \times 10^3$ | $7.117 \times 10^8$ | $1.635 \times 10^4$ | $8.330 \times 10^3$ | $8.894 \times 10^9$ | $2.331 \times 10^9$ | $4.057 \times 10^{10}$ | $5.099 \times 10^9$ |
| 5 | $7.694 \times 10^2$ | $8.357 \times 10^2$ | $6.286 \times 10^7$ | $7.239 \times 10^2$ | $1.299 \times 10^3$ | $1.831 \times 10^{10}$ | $4.942 \times 10^7$ | $2.348 \times 10^7$ | $1.587 \times 10^{10}$ |
| 6 | 0 | $5.383 \times 10^3$ | $5.445 \times 10^8$ | 0 | $2.074 \times 10^2$ | $1.285 \times 10^{10}$ | $7.259 \times 10^5$ | $4.206 \times 10^4$ | $1.405 \times 10^9$ |
| 7 | 0 | $4.156 \times 10^2$ | $1.299 \times 10^4$ | 0 | $5.62 \times 10^2$ | $6.795 \times 10^9$ | $6.320 \times 10^4$ | $8.241 \times 10^3$ | $1.823 \times 10^8$ |
| 8 | 0 | 0 | $6.214 \times 10^2$ | 0 | 0 | $5.318 \times 10^7$ | $5.867 \times 10^3$ | $7.542 \times 10^3$ | $7.771 \times 10^7$ |
| 9 | 0 | 0 | 0 | 0 | 0 | $7.358 \times 10^3$ | 0 | $3.111 \times 10^2$ | $6.282 \times 10^2$ |
| 10 | 0 | 0 | 0 | 0 | 0 | 0 | 0 | 0 | $1.326 \times 10^2$ |
| Bacterium isolation positive rate (%) | 50 | 70 | 80 | 50 | 70 | 90 | 90 | 90 | 100 |

Note:
values in the table are the average of the ascitic colony counts of each mouse, in a unit of CFU/mL.

It can be seen from the results of animal intraperitoneal colony count in Table 5 that, use of N1 to N4 and W in combination with ampicillin can control the ampicillin-resistant bacteria to different extents. When used in combination with AMP, N1 has the best effect and W has the worst effect. Dose-effect analysis shows that low dose has the poor effect, and there is no significant difference in effect between the medium-dose group and high-dose group.

Considering the data of animal death and animal intraperitoneal bacterial count together as a whole, control groups (that is, normal control group, AMP-resistant bacterium infection model control group and AMP intervention control group thereof, AMP-sensitive bacterium infection model control group and AMP intervention control group thereof) were designed as a quality control system in the experiment, mortalities of animals in the model control group are above 90%, indicating that the model is constructed successfully. Meanwhile, the animals of the AMP-sensitive bacterium infection model were protected effectively, while the animals in the AMP-resistant bacterium infection model-AMP intervention control group cannot be protected, indicating that the experimental system is normal.

The experiment analyzes the therapeutic effect of AMP in combination with N1 to N4 and W mainly through the data of animal death and bacterial count, the data show that, when N1 to N4 and W are used in combination with AMP, N1 to N4 can effectively protect the animals of the experimental AMP-resistant bacterium infection model from death, indicating that the test sample changes the sensitivity of the experimental bacteria to antibiotics, wherein N1 has the most prominent effect, and N4 has the worst effect, which indicates that the content of the secologanic acid in the honeysuckle extract has significantly positive correlation with the effect; Meanwhile, the experiment exhibits a good dose-effect relationship, that is, the effect of high-dose and medium-dose is significantly better than that of low-dose. Although W also shows a certain effect, the effect is significantly inferior to that of the extract.

What is claimed is:

1. A pharmaceutical composition for preventing and/or treating a disease caused by a bacterium, comprising a honeysuckle extract containing iridoid compounds and an antibiotic; wherein the honeysuckle extract contains secologanic acid represented by the following structural formula (1):

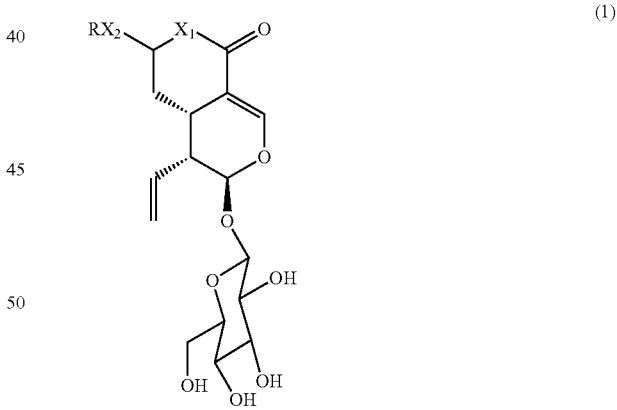

wherein in formula (1), $X_1$ and $X_2$ each independently represent O, and R represents H;
wherein the honeysuckle extract contains 50 wt % or more of secologanic acid represented by formula (1);
wherein the preventing and/or treating a disease caused by a bacterium is achieved by reversing resistance of bacteria;
wherein the antibiotic is ampicillin and/or erythromycin, and the antibiotic is greater in weight amount than that of the honeysuckle extract; and
wherein the honeysuckle extract is prepared by a method comprising the following steps:

(1) pulverizing honeysuckle (*Lonicera japonica*), and extracting the pulverized honeysuckle with water and/or $C_1$-$C_6$ alkyl alcohol aqueous solution containing not more than 95% alcohol by volume to obtain an extract;

(2) concentrating the extract obtained in step (1) under normal or reduced pressure to obtain an extractum, or performing spray-drying on the extract obtained in step (1) to obtain a powder, and dissolving the extractum or powder with water, then carrying out precipitation or settlement with $C_1$-$C_6$ alkyl alcohol aqueous solution containing not more than 95% alcohol by volume to obtain a precipitate or a dissolving liquid concentrate;

(3) isolating and purifying the precipitate or dissolving liquid concentrate obtained in step (2) by chromatography, and collecting eluent containing iridoid compounds, wherein the chromatography is selected from one or more of macroporous adsorption resin column chromatography, normal phase silica gel chromatography and reversed phase silica gel chromatography.

2. The pharmaceutical composition according to claim 1, wherein the pharmaceutical composition further comprises a pharmaceutically acceptable carrier and/or excipient.

3. A pharmaceutical kit for preventing and/or treating a disease caused by a bacterium, comprising a honeysuckle extract containing iridoid compounds and an antibiotic which are placed separately;

wherein the honeysuckle extract contains secologanic acid represented by the following structural formula (1):

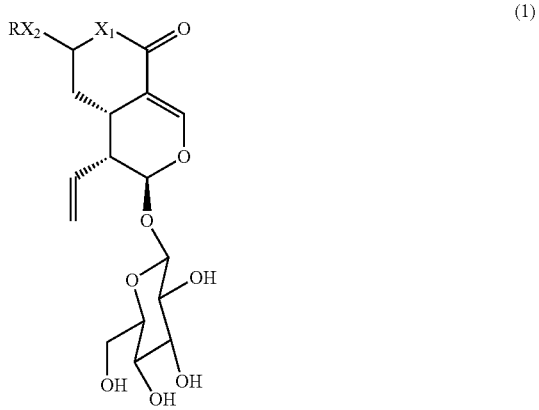

wherein, $X_1$ and $X_2$ each independently represent O, and R represents H; and wherein the honeysuckle extract contains 50 wt % or more of secologanic acid represented by formula (1), wherein preventing and/or treating a disease caused by a bacterium is achieved by reversing resistance of bacteria;

wherein the antibiotic is ampicillin and/or erythromycin, and the antibiotic is greater in weight amount than that of the honeysuckle extract; and wherein the honeysuckle extract is prepared by a method comprising the following steps:

(1) pulverizing honeysuckle (*Lonicera japonica*), and extracting the pulverized honeysuckle with water and/or $C_1$-$C_6$ alkyl alcohol aqueous solution containing not more than 95% alcohol by volume to obtain an extract;

(2) concentrating the extract obtained in step (1) under normal or reduced pressure to obtain an extractum, or performing spray-drying on the extract obtained in step (1) to obtain a powder, and dissolving the extractum or powder with water, then carrying out precipitation or settlement with $C_1$-$C_6$ alkyl alcohol aqueous solution containing not more than 95% alcohol by volume to obtain a precipitate or a dissolving liquid concentrate;

(3) isolating and purifying the precipitate or dissolving liquid concentrate obtained in step (2) by chromatography, and collecting eluent containing iridoid compounds, wherein the chromatography is selected from one or more of macroporous adsorption resin column chromatography, normal phase silica gel chromatography and reversed phase silica gel chromatography.

4. The pharmaceutical composition according to claim 1, wherein the honeysuckle extract contains 70 wt % or more of secologanic acid.

5. The pharmaceutical composition according to claim 1, wherein the honeysuckle extract contains 80 wt % or more of secologanic acid.

6. The pharmaceutical composition according to claim 1, wherein the honeysuckle extract contains 90 wt % or more of secologanic acid.

7. A method of treating a disease caused by a bacterium in a subject in need thereof comprising administering to the subject an effective amount of the pharmaceutical according to claim 1, wherein the bacterium is an ampicillin-resistant, erythromycin-resistant bacterium, and/or multiple antibiotic-resistant bacterium.

8. The method according to claim 7, wherein the bacterium is a gram-negative bacterium, and wherein gram-negative bacterium is an ampicillin-resistant *Escherichia coli, Pseudomonas aeruginosa*, and/or *Klebsiella pneumoniae*.

* * * * *